United States Patent [19]

Sheu et al.

[11] Patent Number: 5,417,950

[45] Date of Patent: May 23, 1995

[54] PROCESS FOR THE PURIFICATION OF NITRIC OXIDE

[75] Inventors: Lien-Lung Sheu, Scotch Plains; Martin Bülow, Basking Ridge, both of N.J.

[73] Assignee: The BOC Group, Inc., New Providence, N.J.

[21] Appl. No.: 271,688

[22] Filed: Jul. 7, 1994

[51] Int. Cl.⁶ .......................... B01J 8/02; C01B 21/24
[52] U.S. Cl. ................. 423/239.2; 423/405; 95/128; 95/129; 95/902
[58] Field of Search .............. 423/239.2, 405; 95/47, 95/274, 902, 128, 129; 424/600, 718

[56] References Cited

U.S. PATENT DOCUMENTS

| | | | |
|---|---|---|---|
| 2,568,396 | 9/1951 | James | 432/400 |
| 3,489,515 | 1/1970 | Jockers et al. | 95/187 |
| 3,674,429 | 7/1972 | Collins | 423/239.2 |
| 4,149,858 | 4/1979 | Noack et al. | 95/110 |
| 4,153,429 | 5/1979 | Matthews et al. | 95/117 |

*Primary Examiner*—Michael Lewis
*Assistant Examiner*—Thomas G. Dunn, Jr.
*Attorney, Agent, or Firm*—Coleman R. Reap; Larry R. Cassett

[57] ABSTRACT

A gas mixture comprised of nitric oxide and, optionally an inert gas, and containing small amounts of nitrogen dioxide, and perhaps moisture and sulfur dioxide, is purified by passing the gas stream through a bed of metal cation-free alumina-deficient zeolites of types Y or ZSM-5. The concentrations of nitrogen dioxide, sulfur dioxide and moisture in the gas stream are reduced to about 1 ppm or less as the gas mixture passes through the bed of zeolite.

26 Claims, No Drawings

PROCESS FOR THE PURIFICATION OF NITRIC OXIDE

FIELD OF THE INVENTION

The present invention is directed to a process for purifying nitric oxide, and more particularly to a process in which nitrogen dioxide is removed from nitric oxide by adsorption.

BACKGROUND OF THE INVENTION

Nitric oxide has recently been found to play an important role in life processes in humans and animals. For example, it helps maintain blood pressure by dilating blood vessels, and kills foreign invaders in the body's immune system. Studies indicate that extraordinary benefits may be obtained by administering small dosages of nitric oxide to patients who suffer from certain illnesses or diseases. Of particular interest is the prospect of reducing pulmonary vasoconstriction in pediatric patients with congenital heart disease complicated by pulmonary artery hypertension by having the patients inhale oxygen-enriched air containing very small concentrations of nitric oxide.

Nitric oxide is a relatively stable gas when it is in the pure state or mixed with an inert gas, such as nitrogen or argon. However, when it is mixed with oxygen it reacts rapidly with the oxygen to form nitrogen dioxide, a substance that is highly toxic to humans. The nitrogen dioxide reacts with water to form nitric and nitrous acids, which, when inhaled can cause severe pulmonary oedema, acid pneumonitis or even death. Because of the highly toxic character of nitrogen dioxide, nitric oxide that is intended for inhalation use by humans is generally purified to remove any nitrogen dioxide that is initially in the nitric oxide product as a result of the manufacturing process, and the purified product is stored and shipped in an oxygen-free environment to prevent the subsequent generation of nitrogen dioxide in the storage or shipping container.

Nitric oxide is generally administered to a patient by diluting a nitrogen-nitric oxide concentrate gas containing about 1000 ppm nitric oxide with oxygen or oxygen-enriched air carrier gas to produce an inhalation gas containing nitric oxide in the desired concentration range (usually about 0.5 to 200 ppm, based on the total volume of the inhalation gas). Calculations based on nitric oxide chemical kinetics suggest that if pure oxygen is mixed with the above-described nitrogen-nitric oxide concentrate to produce a gas mixture having a nitric oxide concentration of 200 ppm, it takes only about 3 seconds for the concentration of nitrogen dioxide in the gas mixture to build up to 3 ppm. The currently accepted upper limit for nitrogen dioxide inhalation is 5 ppm (based on the total volume of breathing gas being inhaled). Assuming that this gas mixture is inhaled by a patient within 3 seconds after mixing the nitrogen-nitric oxide concentrate and oxygen, the amount of nitrogen dioxide initially present in the nitric oxide-nitrogen concentrate would have to be very low to ensure that the nitrogen dioxide concentration in the inhalation gas does not exceed 5 ppm. To minimize the risk of exceeding the 5 ppm upper limit, it is desirable that the concentration of nitrogen dioxide in the nitrogen-nitric oxide supply vessel be as low as possible, and it is most preferred that it not exceed about 1 ppm.

Nitrogen dioxide is produced as a byproduct of most, if not all, nitric oxide production processes. Various techniques are employed to remove nitrogen dioxide from the nitric oxide. U.S. Pat. No. 3,489,515 discloses the purification of nitric oxide by washing the nitric oxide with a dilute aqueous solution of nitric acid. The water reacts with the nitrogen dioxide to produce nitric and nitrous acids, which can be washed from the gaseous product stream by washing the stream with water. This method is not satisfactory for producing medical grade nitric oxide because it does not adequately reduce the concentration of nitrogen dioxide in the product gas stream. Nitrogen dioxide can also be removed from nitric oxide by cryogenic distillation. This method likewise leaves a lot to be desired because of the high capital cost of distillation equipment and because not all of the valuable nitric oxide is recovered during the distillation.

Another purification technique that has been reported is adsorption using as adsorbent a bed of activated coke or activated charcoal (see U.S. Pat. Nos. 2,568,396 and 4,149,858). This procedure suffers from the disadvantages that the activated coke and activated charcoal do not efficiently remove nitrogen dioxide from the gas stream, they adsorb more nitric oxide than is desired and they tend to catalyze the disproportionation of nitric oxide to nitrogen dioxide and nitrogen.

It is known that certain zeolites preferentially adsorb nitrogen dioxide from gas streams containing nitric dioxide and nitrogen dioxide. For example, U.S. Pat. No. 4,153,429, issued to Matthews et al, which relates to the removal of $NO_x$ from gas streams, discloses the use of zeolite Y adsorbent containing 8 to 30 equivalent percent metal cations to remove nitrogen dioxide from a gas mixture. The patentees assert that zeolites do not adsorb nitric oxide, and to eliminate nitric oxide from the gas mixture, stoichiometric quantities of oxygen must be present with respect to the quantity of nitric oxide to be removed from the gas stream. Nitric oxide is oxidized to nitrogen dioxide in the presence of oxygen.

Copending U.S. patent application Ser. No. 129,467, filed Sep. 30, 1993, discloses the removal of nitrogen dioxide from a nitric oxide gas stream by passing the gas stream through a zeolite selected from types A, X and Y zeolites, mordenite, faujasite and chabazite. Although these adsorbents exhibit superior nitrogen dioxide adsorption properties it has been found that they also possess the undesirable attribute of catalyzing the disproportionation of nitric oxide to nitrogen dioxide and nitrogen. It is believed that the metal cations on the zeolite cause the catalytic reaction.

Zeolites, such as type A, X and Y zeolites, and other adsorbents which may adsorb nitrogen dioxide, such as silica and alumina, also possess the characteristic of removing water vapor from a gas stream passing through them. This is an undesirable attribute if the gas stream being purified is intended for use as an inhalant for patients in medical applications, since the absence of moisture in the inhaled gas stream tends to cause drying and irritation of the patient's air passages.

When administering NO-containing gas streams to human patients, it is desirable that very little or no NO in the gas stream be converted to $NO_2$, not only because of the toxicity of $NO_2$ to humans, but also because of the importance of administering an accurate dosage of NO to the patient. It is also desirable to minimize the amount of moisture adsorbed from the inhalant gas being administered to the patient, to avoid drying of the patient's air passages. The present invention provides a simple and efficient method of achieving both of these objectives.

SUMMARY OF THE INVENTION

In one embodiment of the invention, a nitric oxide gas stream containing one or more impurities, including nitrogen dioxide, is purified by passing the gas stream through a bed of one of certain metal cation-depleted molecular sieves which preferentially adsorb nitrogen dioxide relative to nitric oxide, oxygen, nitrogen and water vapor, thereby effecting the removal of nitrogen dioxide from the gas stream without also removing significant amounts of the other mentioned components.

In a preliminary step of the nitric oxide purification procedure of the invention, the concentration of nitrogen dioxide in the gas stream being treated is reduced to a concentration of about 5000 ppm or less by washing the gas stream with dilute nitric acid and/or water and then the washed gas stream is passed through one or more beds of the above-mentioned adsorbents to remove nitrogen dioxide.

In another embodiment, the nitric oxide gas stream is diluted with a sufficient amount of an inert gas, such as nitrogen or argon, to reduce the concentration of nitric oxide in the gas stream to a predetermined concentration, generally in the range of about 5 to about 5000 ppm, and the diluted gas mixture is further purified by passing it through one or more beds of the above-mentioned metal cation-depleted molecular sieves, thereby reducing the concentration of nitrogen dioxide in the diluted gas stream to the desired level.

In a third embodiment, the nitric oxide gas stream is first partially purified by passing it through one or more beds of the above-mentioned metal cation-depleted molecular sieves, thereby reducing the concentration of nitrogen dioxide in the gas stream to a certain desired level, and then the partially purified gas stream is diluted with a sufficient amount of an inert gas, such as nitrogen, argon or helium, to reduce the concentration of nitric oxide in the gas stream to the desired final concentration, generally about 5 to about 5000 ppm.

In a most preferred embodiment of the invention, a nitric oxide-inert gas mixture is first blended with an oxygen-containing gas, which may be substantially pure oxygen or an oxygen-inert gas mixture, such as air or oxygen-enriched air, to reduce the nitric oxide to the desired level, usually about 1 to about 200 ppm. The resulting mixture is then passed through one or more beds of the above-mentioned metal cation-depleted adsorbents, thereby reducing the nitrogen dioxide concentration in the gas mixture to the desired level, generally not more than about 3 ppm. In this embodiment, the gas stream may be humidified before, during or after the oxygen blending step.

The conditions under which the adsorption is carried out are not critical. In general, it can be carried out at temperatures in the range of about $-50°$ to about $300°$ C. or higher, and at absolute pressures in the range of about 0.5 to about 200 bar or higher. To simplify the process, the adsorption is preferably carried out at temperatures in the range of about $0°$ to about $100°$ C. and at absolute pressures in the range of about 1 to about 10 bar.

The adsorption can be carried out in a single bed of adsorbent or in a battery of two or more adsorption beds arranged in parallel and/or in series, the parallel arranged beds being operated out of phase, so that at least one bed is undergoing adsorption while the adsorbent in another bed is being replaced or regenerated.

In the above processes the concentration of nitrogen dioxide in the purified gas stream is reduced to any desired level, typically not more than about 700 ppm, preferably not more than about 10 ppm, and most preferably not more than about 3 ppm.

DETAILED DESCRIPTION OF THE INVENTION

The nitric oxide that is purified by the process of the invention can be produced by any of several well known manufacturing methods. According to one method, sulfur dioxide and nitric acid are reacted in the presence of water to produce the nitric oxide. A number of byproducts, including sulfuric acid, nitrous oxide (laughing gas) and nitrogen dioxide are produced in this process. The raw product stream also contains unreacted sulfur dioxide. The sulfuric acid is easily removed from the product gas by phase separation followed by water wash. The nitrous oxide does not interfere with the use of the nitric oxide in an inhalation gas since it has a very low toxicity. However, as explained above, nitrogen dioxide, and sulfur dioxide, must be substantially completely removed from the product gas because of the extreme toxicity of these compounds. When the gas being purified is to be stored, moisture is also desirably removed to avoid corrosion problems.

Nitric oxide can also be produced by combusting ammonia with oxygen at temperatures of about $1000°$ C. Byproducts of this process include nitric acid, nitrous acid, nitrous oxide, nitrogen dioxide and nitrogen. The nitric and nitrous acids can be removed by water washing the product gas. Significant quantities of nitrogen dioxide can be removed from the product gas by water washing it with dilute nitric acid obtained as a by-product, and subsequently washing the product gas with substantially pure water. Since this process uses oxygen (or air) as a reactant, and since nitric oxide reacts with oxygen to produce nitrogen dioxide, care must be taken to ensure that all of the oxygen is consumed in the reaction. This can be accomplished by conducting the combustion in the presence of excess ammonia.

A third method of producing nitric oxide is by subjecting air to a high voltage electric arc. This procedure is convenient for on site production of small quantities of nitric oxide. Side products which must be removed from the nitric oxide produced by this method include nitrogen dioxide and ozone.

The nitric oxide-rich gas product made by the above processes may contain nitrogen, depending upon which process is used. This poses no problem with respect to the use of the nitric oxide product in inhalation therapy, because nitrogen is nontoxic and is generally used as a diluent for the nitric oxide. The nitric oxide gas is, however, stored in an oxygen-free environment. In the context of this invention "oxygen-free" means that the nitric oxide product contains no more than about 10 ppm oxygen. It is important to prevent oxygen from coming into contact with the nitric oxide gas product during storage, since oxygen readily reacts with nitric oxide to form nitrogen dioxide.

The adsorbents used in the process of the invention are substantially metal cation-free and alumina-deficient, i.e. their lattice structures are substantially free of alumina groups. Specifically, they have silicon to aluminum atomic ratios of at least 100. Included in this group of adsorbents are molecular sieves of the FAU, MFI and MEL type structures, including zeolites that have been made alumina-deficient by dealumination and molecular sieves that are directly synthesized without introducing alumina groups into the lattice structure. Alumina-deficient molecular sieves useful in the invention include dealuminated type Y zeolite (DAY), ZSM-5, ZSM-11 and ZMS-20, all having silicon to aluminum atomic ratios of at least about 100. Other synthesized molecular sieves that are substantially free of alumina groups which are useful in the invention include those having structures analogous to ZSM-5 and ZSM-11, known as silicalite-1 and silicalite-2, respectively, each of which are substantially free of alumina groups in their structures. Preferred molecular sieves are DAY, alumina-deficient ZSM-5 and silicalite-1, all of which are substantially metal cation-free and all of which are commercially available. For purposes of this invention the term "metal cation-free" means that the adsorbent contains no more than trace amounts of metal cations, and the terms "alumina-deficient" and "dealuminated", when used in reference to molecular sieves mean that the ratio of silicon to aluminum atoms in the sieves is at least about 100:1, i.e., the ratio of silica to alumina groups in the sieve is at least 200:1.

Alumina-deficient molecular sieves can be prepared, for example, by steaming or acid washing a zeolite of the desired structure, or by treating the zeolite with silicon tetrafluoride and ammonium thiosilicate, any of which procedures results in the manufacture of a molecular sieve having a crystalline structure comprised substantially of tetrahedral silicon dioxide units. The particular method of dealumination of the adsorbents to be used in the invention is not critical and methods of effecting the desired result are well known and form no part of the present invention.

The metal cation content of the molecular sieves from which the adsorbents to be used in the invention are made can also be decreased by replacing the metal cations with hydrogen ions, i.e. protons. This can be accomplished, for example, by replacing metal cations with ammonium ions and subsequently driving ammonia from the exchanged adsorbent, thereby leaving protons in place of the metal cations. This procedure is likewise well known and forms no part of the present invention. If desired, the metal cation content of the precursor molecular sieves can be reduced by a combination of the above two procedures, that is, by increasing the silica-to-alumina ratio in the adsorbent and by replacing some or all of the remaining metal cations with protons.

As indicated above, the conditions under which the adsorption process of the invention is carried out are not critical. The adsorption can be carried out at any temperature below the decomposition temperature of the nitric oxide product and the adsorbent, and it is generally carried out at the temperature which provides optimum separation. In purifying crude nitric oxide product it is often preferred to conduct the adsorption process at a temperature which is congruous with other steps of the product manufacturing process, and it is particularly preferred to conduct the adsorption at normal ambient temperatures and pressures, if possible. Those skilled in the art can easily determine which operating conditions are best suited for their purposes.

When the nitric oxide product gas is prepared for use as an inhalation gas it is often preferred to dilute the product gas with an oxygen-free inert gas which is nontoxic to humans to produce a less concentrated gas mixture which can later be easily blended with oxygen or oxygen-enriched air to make up an inhalation gas having the desired concentration of nitric oxide. Suitable diluent gases include nitrogen, argon, helium, etc. The preferred diluent gas is nitrogen because of the ready availability and low cost of this gas. The nitric oxide-rich gas is preferably diluted with the oxygen-free inert gas to a concentration such that it can be conveniently blended with the oxygen or oxygen-enriched gas that is used to make up the inhalation gas. Typical inert gas-nitric oxide gas mixtures contain about 5 to about 5000 ppm nitric oxide. Preferred mixtures contain about 5 to about 2000 ppm nitric oxide. The inert gas-nitric oxide mixture can later be blended with oxygen or oxygen-enriched air having an oxygen concentration that will provide the desired oxygen to nitric oxide ratio (usually in the range of about 0.5 to about 200 ppm nitric oxide) and the desired oxygen to nitrogen concentration ratio.

The process of the invention has several important applications. It can be used to directly purify a nitric oxide-rich gas, such as the product obtained from any of the above manufacturing processes. It can also be used to purify an inert gas-nitric oxide concentrate prepared from the nitric oxide-rich gas and an inert gas, as described above. In each of the above cases, the process is effective to reduce the concentration of nitrogen dioxide in the purified gas to any desired level. It is often advantageous to purify the nitric oxide-rich gas prior to dilution, because the volume of gas passing through the bed of adsorbent will be much smaller than if it is first diluted with inert gas, and the adsorption process can be easily operated to reduce the nitrogen dioxide content to low concentrations and subsequent dilution of the nonadsorbed gas product will lower the concentration of nitrogen dioxide in the inert gas-diluted concentrate to levels well below its desired maximum concentration.

The process of the invention can be practiced in a third very useful way. It can be used to remove nitrogen dioxide from a nitric oxide-containing inhalation gas mixture after it has been mixed with oxygen or an oxygen-rich gas, i.e. just prior to administration to the patient. This application is particularly advantageous in that it permits the removal of nitrogen dioxide from the gas stream without also removing water vapor from the mixture. Use of the above-specified hydrophobic adsorbents avoids the need to rehumidify the inhalation gas mixture after removal of the nitrogen dioxide, which would be the case if hydrophilic adsorbents were used for purification of the oxygen-containing inhalation gas.

The nitrogen dioxide-containing adsorbent can be somewhat regenerated, if desired. However, it is difficult and not cost effective to desorb nitrogen dioxide from the adsorbent; consequently the adsorbent is preferably removed from the adsorption equipment and discarded before its ability to efficiently adsorb nitrogen dioxide begins to diminish.

The invention is further illustrated by the following simulated example in which, unless otherwise indicated, parts, percentages and ratios are on a volume basis. A hypothetical gas purifier which has an ID of 8 inches and a length of 12 inches and which is charged with 10.6 lbs. of dealuminated type Y zeolite (DAY) sold by DEGUSSA AG of Germany under the trade designation Wessalith is used in the hypothetical example. A hypothetical gas stream having an initial composition of 50 ppm nitric oxide, 8 ppm nitrogen dioxide, 10% water vapor, 80% oxygen and the balance nitrogen is passed through the gas purifier during the simulated run. The duration of the simulated run is 120 hours. The projected composition of the gas stream exiting the gas purifier at various times during the run is tabulated in the Table.

TABLE

| Administration Time, hrs | Gas Composition | | | | |
|---|---|---|---|---|---|
| | NO ppm | NO$_2$ ppm | O$_2$ % | H$_2$O % | N$_2$ % |
| 4 | ~48 | <0.1 | 80 | 10 | Bal |
| 24 | ~48 | ~0.5 | 80 | 10 | Bal |
| 72 | ~48 | ~1 | 80 | 10 | Bal |
| 120 | ~48 | ~2 | 80 | 10 | Bal |

An examination of the tabulated results shows that DAY can be expected to efficiently remove nitrogen dioxide from a gas stream without substantial removal of water vapor contained in the gas stream and without substantial disproportionation or reaction of the nitric oxide in the gas stream during the entire gas administration period.

Although the invention has been described with particular reference to a specific hypothetical example, the example is merely representative of the invention and variations are contemplated. For instance, mixtures of two or more of the disclosed adsorbents can be used in a single bed or two or more of these adsorbents can be used in tandem in the process of the invention. The scope of the invention is limited only by the breadth of the appended claims.

What is claimed is:

1. A method of treating a nitric oxide and nitrogen dioxide containing gas stream for administration to human or animal patients comprising passing said gas stream through a bed of metal cation-free adsorbent having a silicon-to-aluminum atomic ratio greater than about 100:1 selected from the group consisting of dealuminated type Y zeolite, type ZSM-5 zeolite, type ZSM-11 zeolite, type ZSM-20 zeolite, silicalite-1, silicalite-2, and mixtures thereof to selectively adsorb the nitrogen dioxide therefrom, and recovering a nitric oxide enriched stream.

2. The method of claim 1, carried out sufficiently to reduce the nitrogen dioxide content of said gas stream to not more than about 700 ppm.

3. The process of claim 1, wherein the enriched gas stream is diluted with inert gas selected from nitrogen, argon and mixtures of these sufficiently to produce a gas mixture containing about 5 to about 5000 ppm nitric oxide.

4. The process of claim 3, further comprising blending said gas mixture with a gas selected from oxygen or oxygen-enriched air to produce a blended mixture containing about 0.5 to about 200 ppm nitric oxide.

5. The process of claim 1, wherein said adsorbent is selected from the group consisting of dealuminated type Y zeolite, type ZSM-5 zeolite, silicalite-1, and mixtures thereof.

6. The process of claim 5, wherein said adsorbent is dealuminated type Y zeolite.

7. The process of claim 1, wherein said gas stream contains moisture.

8. A method for removing nitrogen dioxide from a gas stream containing nitric oxide and nitrogen dioxide comprising passing said gas stream through a bed of substantially metal cation-free adsorbent having a silicon-to-aluminum atomic ratio greater than about 100:1 selected from the group consisting of dealuminated type Y zeolite, type ZSM5 zeolite, type ZSM-11 zeolite, type ZSM-20 zeolite, silicalite-1, silicalite-2, and mixtures thereof to selectively adsorb the nitrogen dioxide therefrom, and recovering a nitric oxide enriched stream.

9. The process of claim 8, wherein said gas stream comprises, nitrogen dioxide, nitric oxide and nitrogen.

10. The process of claim 9, wherein the concentration of nitric oxide in said gas stream is at least 80% by volume.

11. The process of claim 8, wherein said adsorbent is selected from the group consisting of dealuminated type Y zeolite, type ZSM-5 zeolite, silicalite-1, and mixtures thereof.

12. The process of claim 11, wherein said adsorbent is dealuminated type Y zeolite.

13. A method for preparing an inert gas-nitric oxide gaseous product containing about 5 to about 5000 ppm of nitric oxide comprising passing a gas stream containing nitric oxide and nitrogen dioxide through a bed of substantially metal cation-free adsorbent having a silicon-to-aluminum atomic ratio greater than about 100:1 selected from the group consisting of dealuminated type Y zeolite, type ZSM-5 zeolite, type ZSM-11 zeolite, type ZSM-20 zeolite, silicalite-1, silicalite-2, and mixtures thereof to selectively adsorb the nitrogen dioxide therefrom, recovering a nitrogen dioxide-depleted stream, and diluting said nitrogen dioxide-depleted gas stream with said inert gas.

14. The process of claim 13, wherein said nitrogen dioxide depleted gas stream is diluted with said inert gas sufficiently to reduce the concentration of nitrogen dioxide in said gaseous product to not more than about 3 ppm.

15. The process of claim 13, additionally comprising reducing the concentration of nitrogen dioxide in said gas stream to not more than about 5000 ppm prior to passing it through said bed of adsorbent by scrubbing the gas stream with an aqueous liquid, or by subjecting the gas stream to cryogenic distillation or a combination of these procedures.

16. The process of claim 13, additionally comprising reducing the concentration of water vapor in said nitrogen dioxide depleted gas stream to not more than about 20 ppm, 17. The process of claim 13, wherein said gas stream contains one or more impurities selected from sulfur dioxide and ozone and the concentration of said one or more impurities in said gas stream is reduced to not more than about 1 ppm after passing said stream through said absorbent.

18. The process of claim 13, wherein said adsorbent is selected from the group consisting of dealuminated type Y zeolite, type ZSM-5 zeolite, silicalite-1, and mixtures thereof.

19. The process of claim 18, wherein said adsorbent is dealuminated type Y zeolite.

20. The process of claim 13, wherein said inert gas is selected from the group consisting of nitrogen, argon, helium, and mixtures thereof.

21. The process of claim 20, wherein said inert gas is nitrogen.

22. A method for preparing an inert gas-nitric oxide gaseous product containing not more than about 5 ppm of nitrogen dioxide comprising blending a gas stream containing nitric oxide and nitrogen dioxide with sufficient inert gas to reduce the concentration of nitric oxide in the resulting gas mixture to about 5 to about 5000 ppm, passing said gas stream through a bed of substantially metal cation-free adsorbent having a silicon-to-aluminum atomic ratio greater than about 100:1 selected from the group consisting of dealuminated type Y zeolite, type ZSM-5 zeolite, type ZSM-11 zeolite, type ZSM-20 zeolite, silicalite-1, silicalite-2, and mixtures thereof to selectively adsorb the nitrogen dioxide therefrom, and recovering a nitric oxide enriched stream.

23. The process of claim 22, wherein said adsorbent is selected from the group consisting of dealuminated type Y zeolite, type ZSM-5 zeolite, silicalite-1, and mixtures thereof.

24. The process of claim 23, wherein said adsorbent is dealuminated type Y zeolite.

25. The process of claim 22, wherein said inert gas is selected from the group consisting of nitrogen, argon, helium, and mixtures thereof.

26. The process of claim 25, wherein said inert gas is nitrogen.

* * * * *